(12) United States Patent
Motomura et al.

(10) Patent No.: US 7,180,069 B2
(45) Date of Patent: Feb. 20, 2007

(54) RADIATION DETECTOR

(75) Inventors: Hiroshi Motomura, Tokyo (JP); Kazuhiro Saito, Sakado (JP)

(73) Assignees: Nihon Medi-Physics Co., Ltd., Hyogo (JP); Universal Giken Co., Ltd., Kanagawa (JP); SD Giken Co., Ltd., Saitama (JP)

( * ) Notice: Subject to any disclaimer, the term of this patent is extended or adjusted under 35 U.S.C. 154(b) by 155 days.

(21) Appl. No.: 10/490,818

(22) PCT Filed: Sep. 26, 2002

(86) PCT No.: PCT/JP02/09989

§ 371 (c)(1),
(2), (4) Date: Sep. 10, 2004

(87) PCT Pub. No.: WO03/029841

PCT Pub. Date: Apr. 10, 2003

(65) Prior Publication Data

US 2005/0012043 A1    Jan. 20, 2005

(30) Foreign Application Priority Data

Sep. 27, 2001    (JP) ............................... 2001-296255

(51) Int. Cl.
*G01T 1/20* (2006.01)
(52) U.S. Cl. .............................. 250/363.1; 250/361 R; 250/362

(58) Field of Classification Search .......... 250/363.03, 250/361 R, 362
See application file for complete search history.

(56) References Cited

U.S. PATENT DOCUMENTS

| | | | | |
|---|---|---|---|---|
| 3,978,337 A | * | 8/1976 | Nickles et al. | 250/367 |
| 5,014,708 A | * | 5/1991 | Hayashi et al. | 600/436 |
| 5,331,961 A | * | 7/1994 | Inaba et al. | 600/436 |
| 5,811,814 A | * | 9/1998 | Leone et al. | 250/368 |
| 6,295,680 B1 | * | 10/2001 | Wahl et al. | 600/431 |

FOREIGN PATENT DOCUMENTS

| | | |
|---|---|---|
| AT | 393 171 | 8/1991 |
| EP | 0 788 766 | 8/1997 |
| JP | 48-26794 | 8/1973 |
| JP | 57-194374 | 11/1982 |
| JP | 3-238387 | 10/1991 |
| JP | 10-213663 | 8/1998 |

* cited by examiner

*Primary Examiner*—Albert Gagliardi
(74) *Attorney, Agent, or Firm*—Koda & Androlia

(57) ABSTRACT

The present invention provides a radiation detector capable of detecting the radioactive substance accumulated in the tissue inside a body by inserting a detection unit into blood vessels. In the radiation detector of the present invention, comprising a detection unit (2) having a bar-type scintillator (4) which emits light by an incidence of radiation so as to transmit the light from the scintillator through an optical fiber, the detection unit is formed in a size capable of being inserted into the tubules while fine convexoconcaves are provided on the peripheral surface of the scintillator.

4 Claims, 10 Drawing Sheets

RADIATION DETECTOR

TECHNICAL FIELD

The present invention relates to a radiation detector for detecting radiation leakage in tubules and radiation substances present in tissues in the body system. More specifically, it relates to a radiation detector for detecting radiation substances accumulated in the tissues in the body system by inserting a detection unit into a blood vessel of coronary artery and the like after administering a radiopharmaceutical into the body system.

BACKGROUND ART

In the followings, the present invention will be described by referring mostly to its application inside blood vessels. Heart diseases among Japanese has been increasing year after year and it has now grown to be in the second place for the cause of death. Especially, unstable angina pectoris, acute myocardialinfarction, and inschemic heart sudden death are called as acute coronary syndromes, which are very serious diseases. Most of acute coronary syndromes are caused by thrombus formation triggered by a rupture of plaque of coronary artery.

Conventionally, invascular lesions including acute coronary syndromes are examined by nuclear medicine method. Nuclear medicine method is performed by utilizing radiopharmaceuticals accumulated in the subject part of the body, which have been administered beforehand. Diagnoses are carried out by detecting the radiation emitted from the radiopharmaceuticals accumulated in the target area by a detector generally placed outside the body and forming an image based thereon. Although the nuclear medical detection is inferior to CT and MRI as a morphologic diagnosis means, it is superior as a description diagnosis means for functions and tissue of living bodies. Therefore, it has been widely used in clinical examinations. On the other hand, nuclear medicine method devices have been proposed, in which a detector is inserted inside a human body for special purposes. However, these types exhibit a low sensitivity so that they are not used for actual diagnoses. Detectors which can be inserted to narrow blood vessels such as coronary arteries have not been developed so far.

The nuclear medicine method device for performing examinations by placing a detector outside the human body, and the nuclear medicine method device for performing examinations by inserting a detector inside the human body will be described in detail. The former nuclear medicine method device for performing an examination by placing the detector outside the body comprises a detector (in general, a gamma camera) outside the body for detecting the radiation emitted from the radiopharmaceutical administered beforehand and a computer for forming an image based on detected signals. The detector comprises a scintillator and some ten photomultipliers provided inside. Emission of light is caused upon incidence of the radiation to the scintillator emitted from inside the body and the light signals are transmitted to the photomultipliers corresponding to the positions to be converted to electric signals. The signals are formed into images by a computer to be used for diagnoses.

In this nuclear medicine method device, the detector is placed outside the body so that there is a distance between the detector and the target body part. Thus the radiation is scattered and attenuated by the distance and the living body tissue present in between, thereby causing deterioration of the resolution. Also, when the target is the one that is moving such as the heart, deterioration of the resolution cannot be avoided. The maximum resolution is about 5 mm. Therefore, it is impossible to discriminate a very small accumulation of the radiation in the case of, for example, lesions inside the coronary arteries from other radiations. Further, the device is on a large-scale, so that it is very hard to be used in emergency cases such as in a room for the heart catheter where acute coronary syndromes are treated.

There are nuclear medicine method devices in which the detector is miniaturized to be inserted inside the body for a special purpose. However, they are not used practically. As an example of this type of the device, U.S. Pat. No. 4,595,014 discloses an intracavity radiation detector. A collimator formed by a substance such as tungsten is mounted onto the device for obtaining the directivity of the radiation entering into the scintillator. In this case, it is necessary to thicken the collimator especially for the radiation with high energy in order to increase the directivity of the incoming radiation. The volume of the scintillator is reduced and the sensitivity is deteriorated as the thickness of the collimator is increased. Also, the detector of the above-described detection device cannot be inserted into narrow vessels of the living bodies.

As another example of the device in which the detector is inserted inside the body for performing an examination, Japanese Patent Unexamined Publication No. 5-11055 and Japanese Patent Unexamined Publication No. 8-94760 disclose luminal radiation detectors. In these devices, two scintillators with the diameter of about 8 mm are arranged in parallel or in vertical and optical fibers are connected to each scintillator for guiding the light signals to two photomultipliers so as to detect only the coincident signals. Thereby, background is reduced and, at the same time, the directivity of the incoming radiation is obtained. In this method, different light signals by the radiations emitted from different scintillators are coincided so that the background can be reduced. However, the sensitivity for γ-ray becomes low since it is very rare that one photon such as γ-ray makes both scintillator emit the light. Therefore, it is impossible with the method to miniaturize the scintillator to be able to be inserted into the blood vessels.

DISCLOSURE OF THE INVENTION

The present invention has been designed to overcome the forgoing problems. The object of the present invention is to provide a radiation detector which is capable of detecting a radiation leakage of tubules or a radiation substance accumulated in tissue inside a body by inserting a detection unit into the tubules or inside the blood vessels.

In order to achieve the foregoing object, the present invention provides a radiation detector for detecting a radioactive substance present in a tubule, comprising a detection unit having a bar-type scintillator which emits light by an incidence of radiation so as to transmit the light from the scintillator through an optical fiber, wherein the detection unit is formed in a size capable of being inserted into the tubule while fine convexoconcaves are provided on the peripheral surface of the scintillator.

The present invention provides a radiation detector for detecting a radioactive substance present in tissue in a body system, comprising a detection unit having a bar-type scintillator which emits light by an incidence of radiation so as to transmit the light from the scintillator through an optical fiber, wherein the detection unit is formed in a size capable of being inserted into a blood vessel while fine convexoconcaves are provided on the peripheral surface of the scintillator.

In the radiation detector, the sensitivity is deteriorated as the size of the scintillator is reduced. When the radiation goes through the scintillator, there is no emission of light generated. In other words, there is more possibility of the radiation going through the scintillator as the scintillator becomes smaller and the sensitivity becomes deteriorated. In the radiation detector of the present invention, while miniaturizing the scintillator to be able to be inserted into blood vessels, fine convexoconcaves are formed on the peripheral surface for suppressing the sensitivity deterioration due to the reduction of the size. Thereby the reflection of light emitted from inside the scintillator is diffused on the surface of the scintillator to be effectively guided to the optical fiber.

In the present invention, the detection unit is formed in a size capable of being inserted into tubules for detecting the radiation leakage or into blood vessels for examining the presence of lesions. Generally, it is formed in a size which can be inserted into coronary arteries. Specifically, it is desirable that the diameter (thickness) of the scintillator be 1.5 mm or less.

In the present invention, the shape and the like of the fine convexoconcaves are not specifically limited as long as it is capable of diffusing the reflection of light emitted from the inside the scintillator on the surface of the scintillator. Also, the above-described convexoconcaves may be formed in a part of the peripheral surface of the scintillator or on the whole surface. However, it is appropriate to provide them on the whole surface in consideration of improving the sensitivity. There is no limit to the means for forming convexoconcaves on the peripheral surface. However, as an example, the peripheral surface may be polished using, for example, sandpapers.

The radiation detector of the present invention may further comprise the following structures as will be described in the embodiments described later.

① A structure in which a part of the top end face and the peripheral surface of the scintillator is covered by a radiopaque substance.

② A structure in which a rotary moving device is provided for rotating and moving the detection unit back and forth in a tubule or inside a blood vessel.

③ A structure in which, as the optical fiber for transmitting the light from the scintillator, an optical fiber aggregation which is obtained by bundling up thin optical fibers to have substantially the same diameter as that of the scintillator is used.

BEST MODE FOR CARRYING OUT THE INVENTION

Figure 1:
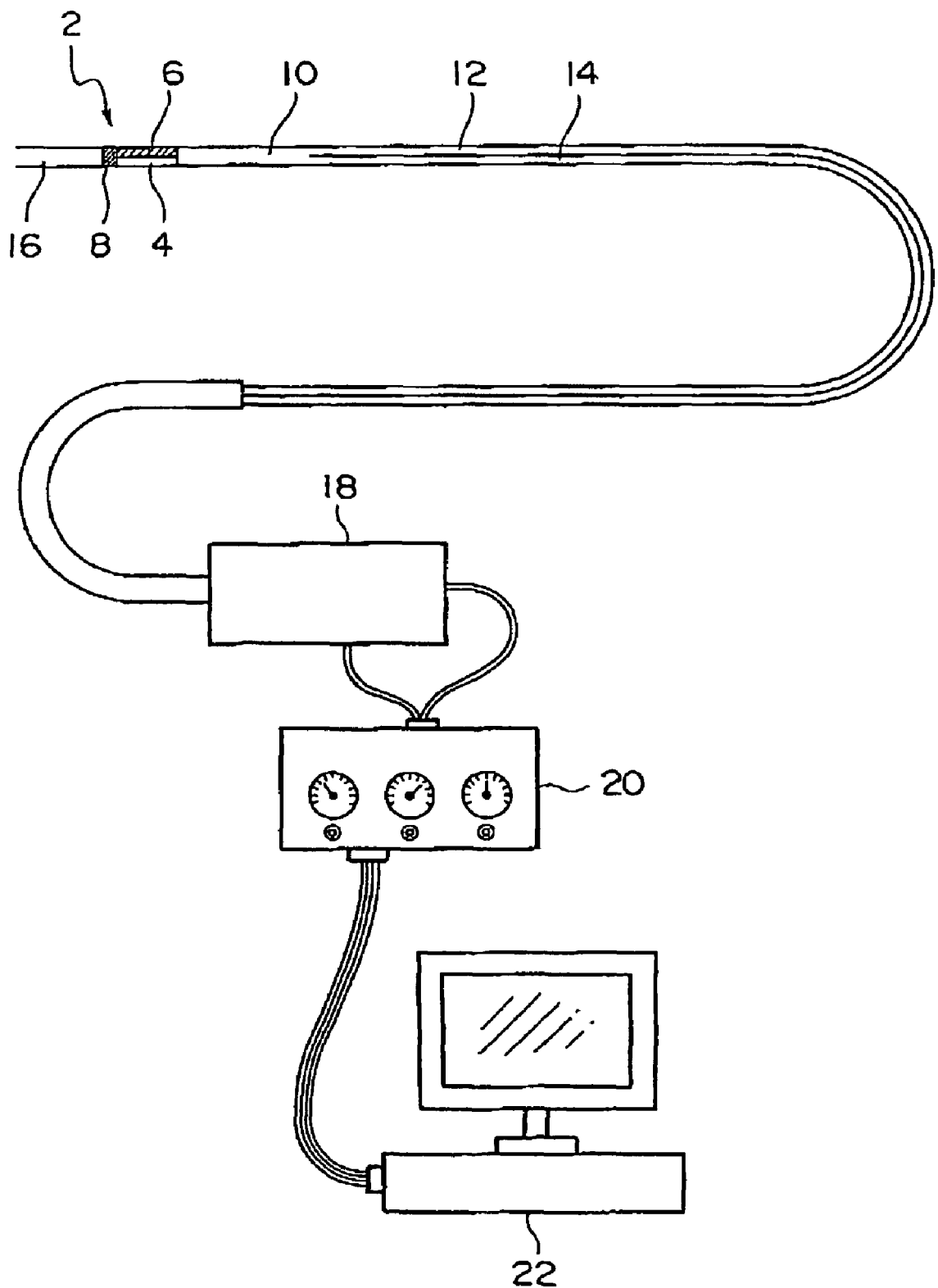
FIG. 1 is a block diagram showing the overall structure of an embodiment of a radiation detector according to the present invention.
Figure 2:
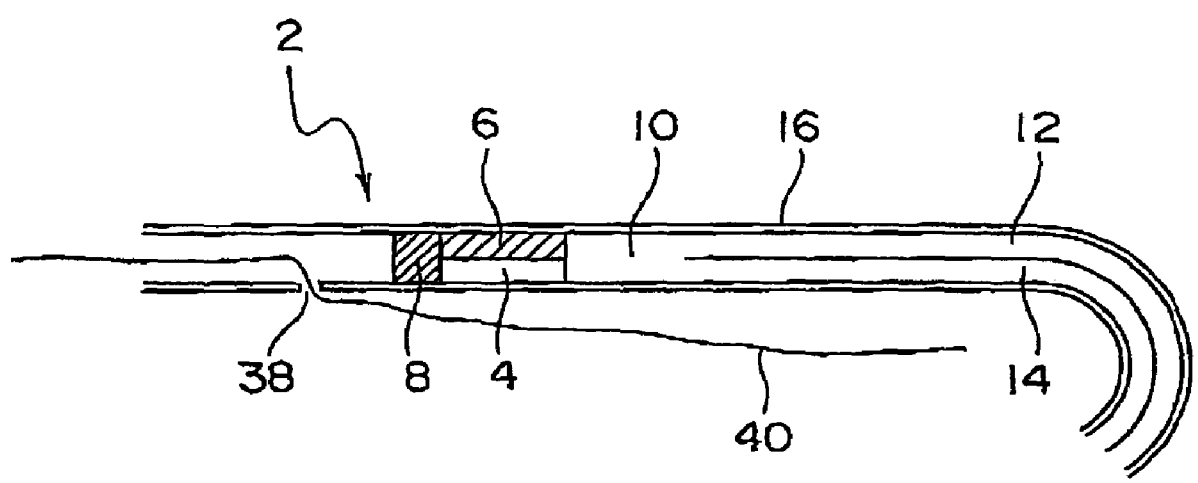
FIG. 2 is an enlarged view of a detection unit in the radiation detector.
Figure 3:
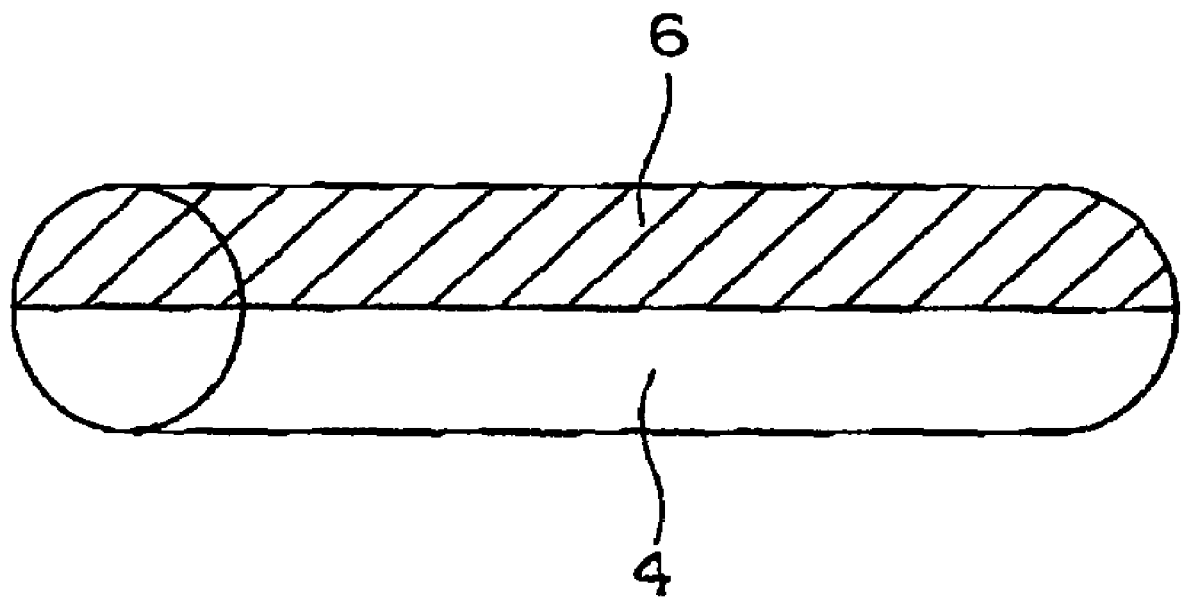
FIG. 3 is an enlarged perspective view of a scintillator of the detection unit.
Figure 4:
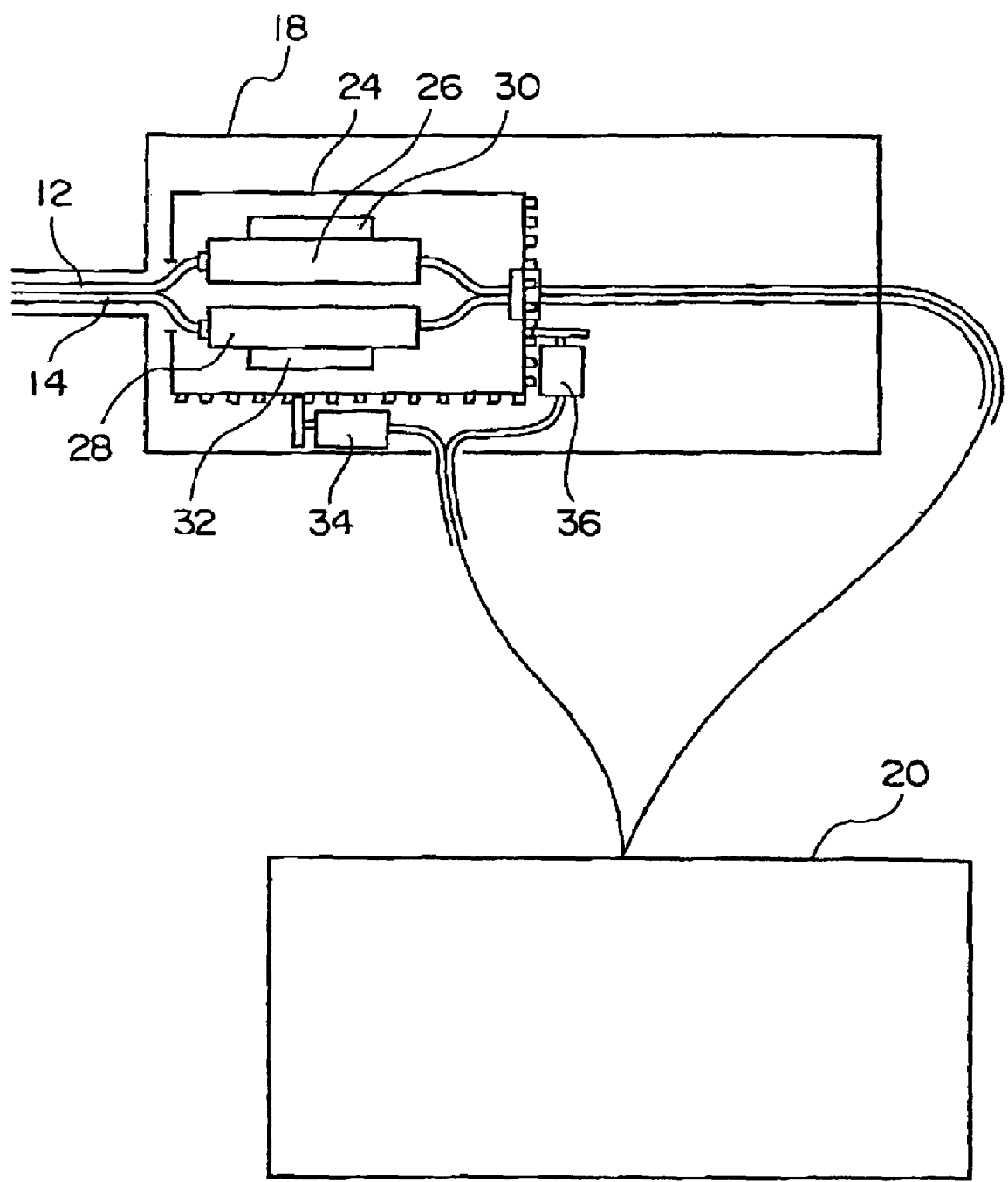
FIG. 4 is a schematic view showing the structures of the rotary moving device and the instrument of the radiation detector.

Embodiments of the present invention will be described by referring to accompanying drawings. However, the present invention is not limited to the embodiments described below. FIG. 1 is a block diagram showing the overall structure of an embodiment of a radiation detector according to the present invention and FIG. 2 is an enlarged view of a detection unit in the radiation detector. FIG. 3 is an enlarged perspective view of a scintillator of the detection unit and FIG. 4 is a schematic view showing the structures of the rotary moving device and the instruments of the radiation detector.

In the radiation detector of the embodiment, numeral 2 is a detection unit, 4 is a column-shape scintillator provided in the detection unit, 6 is a radiopaque substance covering a part (almost a half) of the top end face and the peripheral surface of the scintillator 4, 8 is a cylindrical X-ray opaque substance mounted onto the top end part of the scintillator, 10 is an optical fiber aggregation connected to the rear end part of the scintillator 4, 12 and 14 are two optical fiber branches, 16 is a tube-type lightproof cover for covering the scintillator, the optical fiber aggregation, the optical fiber branches and the like.

The above-described scintillator 4 is formed of plastic scintillator with the diameter of about 1.00 mm and the length of 5.00 mm, cesium iodide, BGO, YAP (Ce) and the like, and fine convexoconcaves are formed on the peripheral surface. The above-described optical fiber aggregation 10 is formed by bundling up a number of optical fibers of about 20 μm in diameter to have almost the same diameter as that of the scintillator 4. Examples of beta-ray or gamma-ray opaque substance 6 are tungsten, tantalum, gold, silver and the like. Examples of the X-ray opaque substance are tungsten, tantalum, copper alloy, stainless steel and the like and examples of the materials for the lightproof cover 16 are stainless steel, lightshield plastic and the like.

Further, in the radiation detector of the embodiment, numeral 18 is a rotary moving device, 20 is a controller and 22 is a computer. The rotary moving device 18 is for rotating and moving the detection unit 2 both at a constant speed inside the blood vessel. An instrument 24 is enclosed inside the rotary moving device 18 and the instrument 24 comprises two photomultipliers 26, 28 and respective amplifiers 30, 32. Further, provided in the rotary moving device 18 are a moving motor 34 for moving the detection unit 2 back and forth by moving the instrument 24 back and forth, and a rotary motor 36 for rotating the detection unit 2 by rotating the instrument 24.

The using direction of the radiation detector of the embodiment will be described by referring to an examination of coronary artery lesion as an example. In this case, radiopharmaceuticals which accumulate in the plaque or thrombus inside the coronary arteries are administered to a patient beforehand.

① First, a guide wire is inserted from an inguinal region into a blood vessel and the guide wire is moved further into the coronary artery. Then, guide wire 40 is inserted into a hole 38 provided in the lightproof cover 16 of the detection unit 2 (FIG. 2) and the detection unit 2 is inserted into the vicinity of the tip area of the coronary artery along the guide wire 40.

② The position of the scintillator 4 is checked by the X-ray opaque substance 8 mounted onto the top end of the scintillator 4. The X-ray opaque substance 8 produces a positive image by radiography performed on the coronary artery. Also, the action of the rotary moving device 18 is controlled by the computer 22 so that the position of the scintillator 4 can be identified by the data of the computer 22.

③ Emission of light is caused when the radiation emitted from the blood vessel lesion. The light is transmitted to the optical fiber aggregation 10 connected to the scintillator 4. The optical fiber aggregation 10 is separated into two optical fiber branches 12, 14 so that the light is equally divided into two to be transmitted to the photomultipliers 26, 28. Each light is converted into electric signals in the photomultipliers 26, 28 and amplified to be transmitted to the controller 20.

④ A counter circuit is enclosed inside the controller 20. The signals from the two photomultipliers 26, 28 enter the counter circuit as pulse for obtaining coincidence. By narrowing the time width of the pulse, the accidental coincidence such as background, transmission background and the like can be eliminated so as to count only the signals form the target radiation as much as possible. The count rate is transmitted to the computer 22.

⑤ The computer 22 displays the count rate based on the measurements by time and positions and on the directivity of the radiation on the screen while storing and diagnosing the values. Then, the description of the lesion is recognized according to the radiation accumulated area inside the coronary artery, the degree of the accumulation and the property of the used radiopharmaceutical. Also, the computer 22 together with the rotary moving device 18 activates the motors 34, 36 for controlling the rotation and the movement of the scintillator 4.

The radiation detector of the embodiment exhibits the following effects. The radiopharmaceuticals administered beforehand accumulate in the arteriosclerosis lesion area (plaque or thrombus) inside the blood vessel. The scintillator inserted inside the blood vessel emits light when detecting the radiation emitted from the accumulation. The light is transmitted to the optical fiber in which a number of fibers are bundled up in one to be connected to the scintillator. The optical fiber is divided into two on the midway so that the light is equally divided into two to be transmitted to the photomultipliers. Each light signal is converted to electric signal (pulse) in the two photomultipliers and, at the same time, the electric signals are transmitted to the controller. The controller strictly obtains the coincidence and counts only the signals by the light emitted from the scintillator. At this time, accidental coincidence is avoided by narrowing the time width of the pulse for suppressing the background to minimum. Thereby, it becomes possible to identify the target radiation and detect the small accumulation of the radiation in the lesion area. Also, the rotary moving device can be rotated and moved at a constant speed inside the blood vessel so that it is effective for continuous search for the lesion areas and for identifying the position. The counted values are displayed by time and positions on the computer and the data can be analyzed.

The radiation detector of the embodiment is obtained after investigating each of the following issues: miniaturization of the scintillator; improvement of the sensitivity and reduction of the background; recognition of the directivity of the radiation entering the scintillator; recognition of the position of the scintillator inside the blood vessel; and the device for rotating and moving the scintillator back and forth inside the blood vessel. These issues will be described in the followings.

(1) Miniaturization of Scintillator

Acute coronary syndromes are caused by thrombus formation due to rapture of the plaque inside the coronary artery. In the conventional nuclear medical method, it has not been possible to detect such small dose of radiation accumulated in the plaque or thrombus. The main reason for this may be that the detection unit cannot be provided closely in contact with the lesion area. The embodiment overcomes the above-described problem by miniaturizing the scintillator to be inserted inside the coronary artery. In other words, the inner diameter of the coronary artery is about 3.00 mm in the basal area and about 1.5 mm in the center area in between the periphery. In the radiation detector of the embodiment, the size of the scintillator is miniaturized to have the diameter of about 1.00 mm and the length of about 5.00 mm so that the detection unit can be inserted to the ramification of the coronary artery.

Further, in order to improve the sensitivity of the scintillator by not leaking the light emission by the incidence of the radiation as much as possible and also to effectively transmit the light to the optical fiber, fine convexoconcaves are provided in the peripheral surface of the scintillator so that the light is diffusely reflected inside the scintillator. Conventionally, in order to diffusely reflect the light inside the scintillator in a large size, a method of winding a tape around the scintillator or a method of applying white coating on the surface of the scintillator are employed. However, with the methods, the tape or the coating serves as the shield thereby attenuating the incoming radiation. Also, there is a small space generated in between the tape or the coating and the scintillator so that there causes a loss of the diffused reflection inside the space. Therefore, the above-described methods cannot be employed for the miniaturized scintillator. In the embodiment, a new method is employed in which fine convexoconcaves are provided by directly processing the surface of the scintillator. It is preferable to use plastic or cesium iodide for the material of the scintillator. They can detect gamma-ray such as $^{99m}$Tc, $^{111}$In, $^{123}$I and beta-ray such as $^{89}$Sr, $^{90}$Y, $^{186}$Re.

(2) Improvement of Sensitivity and Reduction of Background

As described, in the radiation detector, it is inevitable that the sensitivity is deteriorated due to the miniaturization of the scintillator as described. The radiation detector of the embodiment has the sensitivity capable of detecting the small dose of radiation accumulated in the lesion area inside the blood vessel even though the scintillator is miniaturized into a size capable of being inserted into the coronary artery. In other words, in the embodiment, some hundreds of extremely thin optical fibers of about 20 μm diameter are bundled up to have almost the same thickness as that of the diameter of the scintillator to be connected to a scintillator. In order to effectively transmit the light of the scintillator to the optical fiber, it is preferable to connect one scintillator to one optical fiber. In the embodiment, some hundreds of optical fibers are bundled up since it is necessary to equally divide the light signal into two for performing coincidence as will be described later. Thus, it is designed to effectively transmit the light of the scintillator to the bundle made up of some hundreds of optical fibers.

When each optical fiber is viewed from the cross section, it comprises a clad (light reflex) on the outer side and a core (optical light guide) on the inner side. In order for the light to be guided to the end inside the core, it is necessary that the angle of incidence to the core is within a specific value, and the incoming light at an angle over the value does not transmit to the end. The embodiment employs the method of diffusely reflect (diffused reflex) the light on the surface of the scintillator as a method for not leaking the light inside the scintillator and for effectively guiding the light to the optical fibers. The advantage of the method is that rays of light at various angles are generated by the diffused reflection thereby increasing the dose of the light entering the angle of incidence of any core. Other example of the method for not leaking the light inside the scintillator to the outside, there is a method of totally reflecting the light on the surface of the scintillator. However, with the method, although attenuation of the light due to the reflection is small, there is no change in the angle of incidence. Therefore, the light entering inside the angle of incidence of the core is limited to some extent.

Further, in the embodiment, in order to reduce the background, a bundle of optical fibers connecting to the scintillator are divided on the way into two for guiding the equally divided light signals into two photomultipliers to obtain coincidence. In other words, the light signal is converted to the electric signal (pulse) and only the timely coincided pulse is counted by the controller as coincidence. It is important in this method to narrow the time width of the pulse as much as possible for not picking up the background. In the embodiment, the lights inside the scintillator diffusely reflect on the surface to be rays of light at various angles so as to be able to enter a number of optical fibers. Also, the two bundles of the optical fibers are arranged to equally divide the light into two so that the time jitter of the light signals entering the two photomultipliers become equal. This enables to narrow the time width of the pulse as much as possible and to obtain the coincidence. Thereby, only the signals by the emission of light from the scintillator are counted. By reducing the background to the minimum as described, it enables to decrease the discrimination level so that the sensitivity can be further improved.

(3) Recognition of Radiation Directivity entering Scintillator

The radiation detector of the embodiment can recognize the direction of the incoming radiation into the scintillator emitted from the lesion area inside the blood vessel. Therefore, in the embodiment, a part of the top end face and the peripheral surface of the scintillator are shielded by a radiopaque substance. Thus, the radiation from inside the body entering the scintillator is extremely decreased due to the shielded part. Also, the scintillator covered by the radiopaque substance can be rotated at a constant speed (for example, 1 rotation/10 seconds). The rotation is connected to the computer and the count of the incoming radiation by each rotation angle is recorded in the computer. Thereby the directivity of the incoming radiation can be obtained. In other words, it can recognize the direction of radiation emitted from the lesion area inside the blood vessel. Thereby, the position of the radiation accumulation can be recognized by the vertical and lateral positional relation when the blood vessel is viewed by a cross section.

(4) Recognition of Scintillator Position inside Blood Vessel

The radiation detector of the embodiment can recognize the position of the scintillator inside the blood vessel. For example, it is possible to always check the position of the scintillator, i.e. how far (some ten mm) from the tip of the coronary artery or how far (some ten mm) from the furcation point to the peripheral. Therefore, in the embodiment, an X-ray opaque substance is mounted onto the top end part of the scintillator. After inserting the scintillator into the blood vessel, the X-ray opaque substance produces an active image by radiography by external irradiation so that the accurate position of the scintillator inside the blood vessel can be obtained.

(5) Device for Rotating and Moving Scintillator Back and Forth in Blood Vessel

The radiation detector of the embodiment comprises a rotary moving device for rotating the detection unit at a constant speed inside the blood vessel and for moving it back and forth at a constant speed. For example, the rotary moving device makes the scintillator, the optical fibers and the two photomultipliers rotate integrally at a constant speed (for example, 1 rotation/10 seconds) and makes them move at a constant speed (for example, 2 mm/10 seconds) by the operation of the motor through the computer control. This method enables to continuously search the accumulated area of the radiation inside the blood vessel and is effective for accurately recognizing the positional relation of the radiation accumulated area.

EXAMPLES

Example 1

Figures 5F, 5G, 5H:
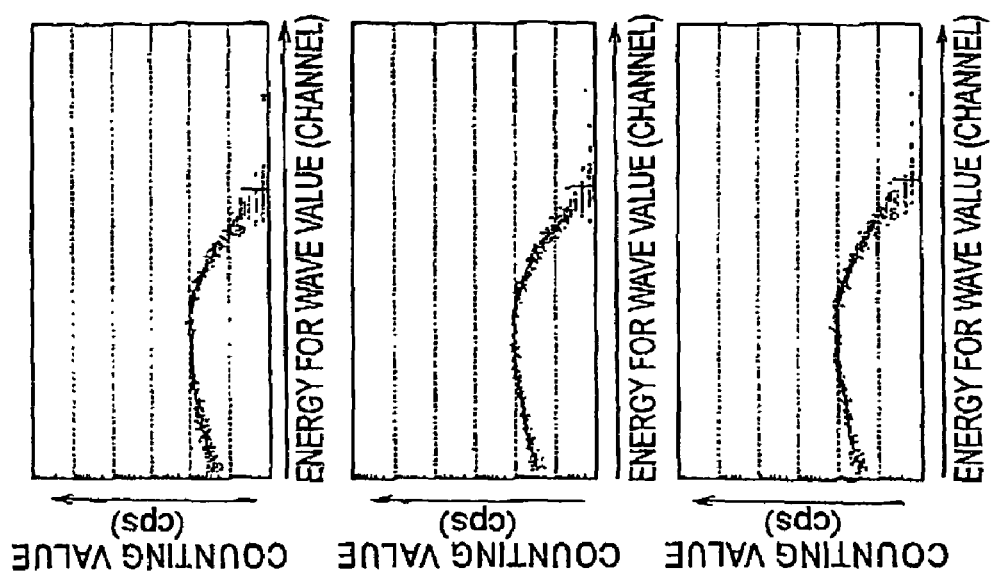
FIGS. 5A to 5C, and 5F to 5H are spectral diagrams showing the pulse height spectra of photomultipliers, respectively.
Figures 5A, 5B, 5C:
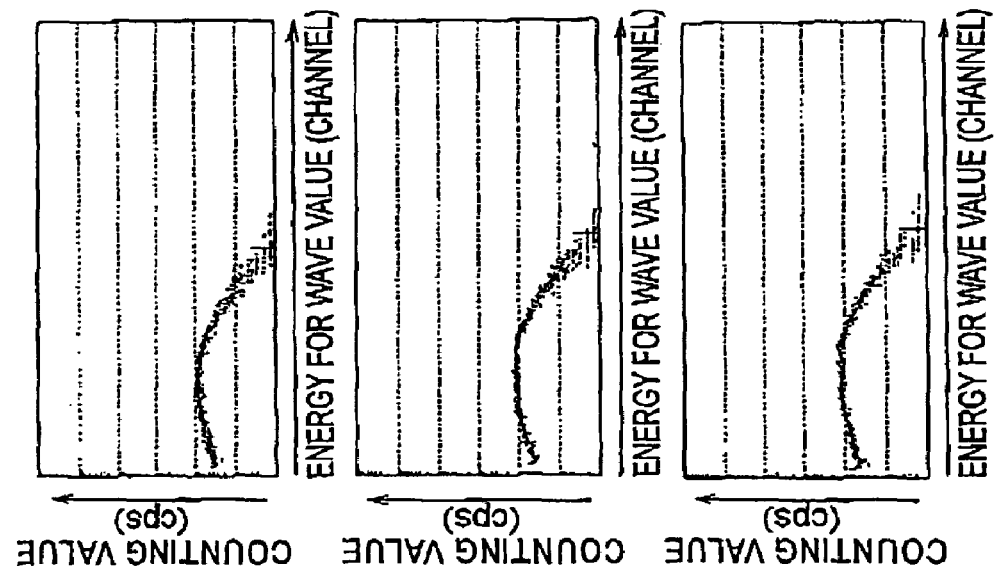
Figure 6D:
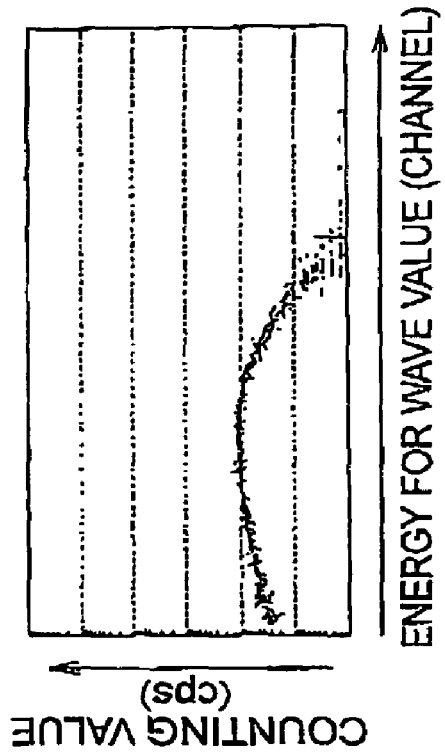
FIGS. 6D, 6E, 6I, and 6J are spectral diagrams showing the pulse height spectra of photomultipliers, respectively.
Figure 6I:
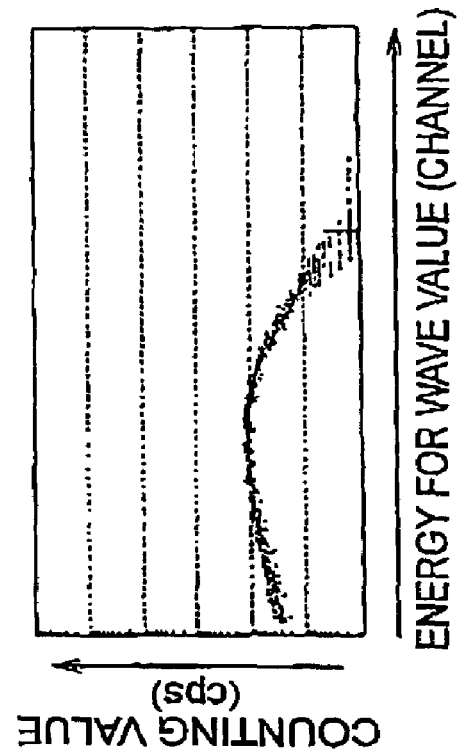
Figure 6E:
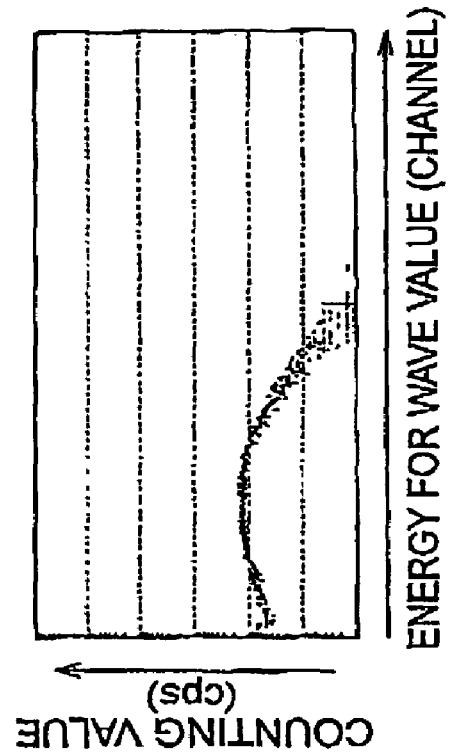
Figure 6J:
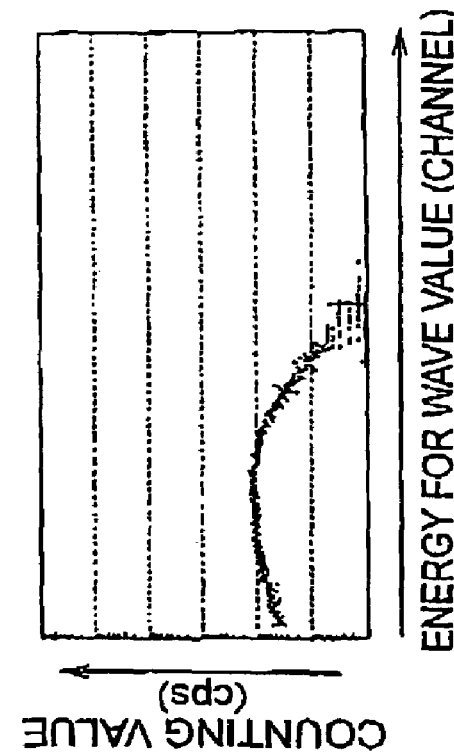
Figure 7:
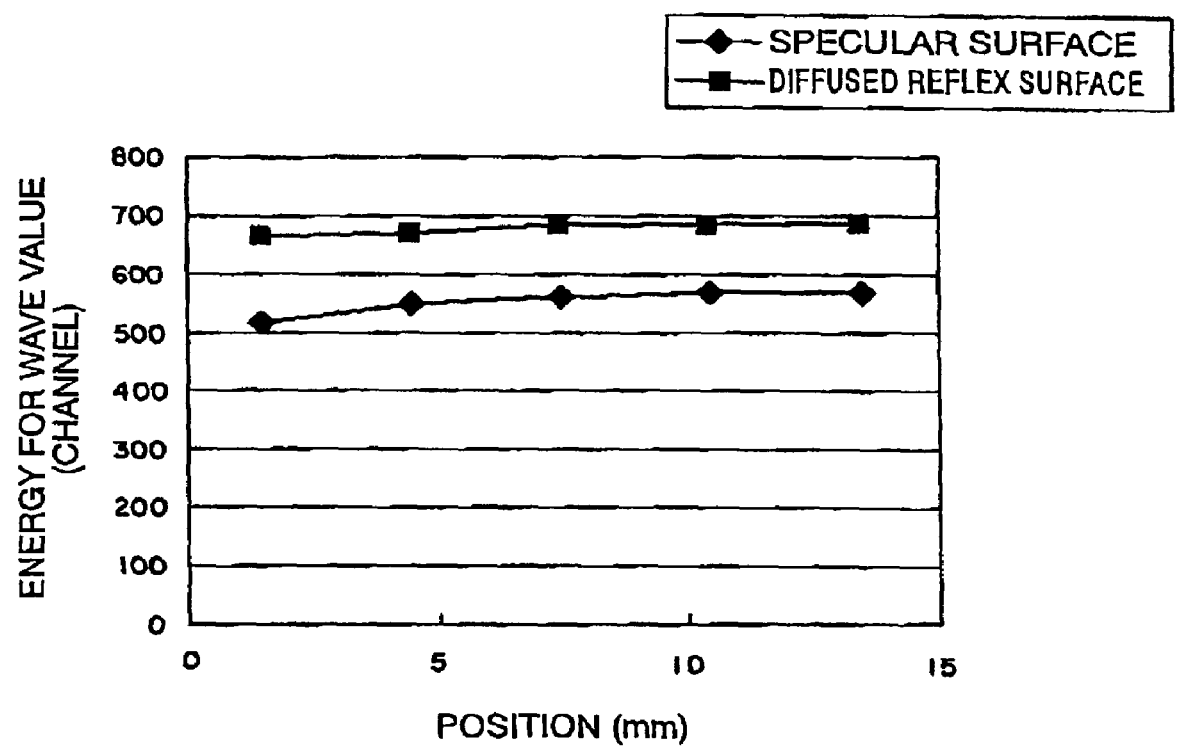
FIG. 7 is a graph showing the maximum wave of the photomultipliers.

Effects of the cases where the peripheral surface of the scintillator was formed to be a specular surface and where it was formed to be a diffused reflex surface (with fine convexoconcaves) were examined. In order to effectively investigate the effects of the surface treatment, a plastic scintillator with the diameter of 3 mm and the length of 15 mm was used. Optical fiber was connected to the basal end face of the scintillator and photomultipliers were connected to the optical fiber. Beta-ray (90Sr—90Y) was used as the radiation source and the radiation source was moved by a collimator with the diameter of 1 mm made of a radiopaque substance from the side face of the scintillator to the axial direction. The photomultiplier pulse height maximum value at this time was measured by a multi-channel analyzer for measuring the channel of the maximum wave. The results of the measurement are shown in FIG. 5 to FIG. 7. The spectral diagrams A to J in FIG. 5 and FIG. 6 show the pulse height spectrum before energy calibration, where the horizontal axis represents the channel showing the energy against the wave value and the vertical axis represents the counting value (cps). In this case, the vertical axis is a logarithmic scale, where the lowest scale is 1, the second lowest is 10, the third lowest is 100, the fourth lowest is 1000, the fifth lowest is 10000, the sixth lowest is 100000, and the top scale (upper end of the horizontal axis) is 1000000. The horizontal axis of the spectral diagrams A to J is a regular scale (linear scale), where the scale in the left end (left end of the vertical axis) is 0 and the scale in the right end (right end of the vertical axis) is 1024. FIG. 7 is a graph showing the energy for the wave value.

TABLE 1

Scintillator Surface: Specular Surface

| Radiation source Position (mm) | Max Channel showing Max Energy for Wave Value | Spectral diagram |
|---|---|---|
| 1.5 | 516 | A |
| 4.5 | 548 | B |
| 7.5 | 560 | C |
| 10.5 | 569 | D |
| 13.5 | 570 | E |

TABLE 2

Scintillator Surface: Diffused Reflex Surface

| Radiation source Position (mm) | Max Channel showing Max Energy for Wave Value | Spectral diagram |
|---|---|---|
| 1.5 | 663 | F |
| 4.5 | 669 | G |
| 7.5 | 686 | H |
| 10.5 | 686 | I |
| 13.5 | 690 | J |

From the results above, it has been verified that the scintillator with the diffused reflex surface can detect the higher wave than the one with the specular surface. This indicates the following: the detection efficiency is improved since the detection count is an integral value of the spectral characteristic; the counting value is improved since the difference of the level (wave value difference) between the electric background increases due to an increase of the wave value so that the count cut by the discriminator becomes less. In other words, it has been verified that the emitted light is effectively transmitted to the photomultipliers.

Example 2

A sensitivity test was performed on the radiation detector shown in FIG. 1 to FIG. 3. In this case, the scintillator was made of plastic with the diameter of 1.0 mm and the length of 5.0 mm. The optical fiber aggregation was prepared by bundling up some tens of optical fibers with the diameter of 40 μm to be in the diameter of 0.8 mm and the length of 2000 mm. The scintillator and the optical fibers were not covered by a lightproof cover so that the test was carried out in a dark field. The test results performed on $^{111}$In as gamma-ray nuclide and $^{89}$Sr as beta-ray nuclide are as follows.

1. Detection Efficiency, Detection Limit

After dropping 3.0 μl radiation source into a dent with the diameter of 2.0 mm and the depth of 1.3 mm formed in an acryl plate, the dent was sealed and the scintillator was set to be in contact with the radiation source sealed area for carrying out the measurement. A set of measurement for 10 seconds was repeated for 10 times and the average was calculated for obtaining the value per second. The results are shown in TABLE 3.

TABLE 3

| | $^{111}$In | $^{89}$Sr |
|---|---|---|
| Background Counting value (cps) | 2.3 | 0.4 |
| Radiation source Counting value (cps) | 36.6 | 1081.1 |
| Radiation source Radiation Value (KBq) | 203.7 | 85.8 |

TABLE 3-continued

| | $^{111}$In | $^{89}$Sr |
|---|---|---|
| Detection Efficiency (%) | 0.018 | 1.260 |
| Detection Limit (Bq) | 14038 | 115 |

2. Verification of Detection Property

Figure 8:
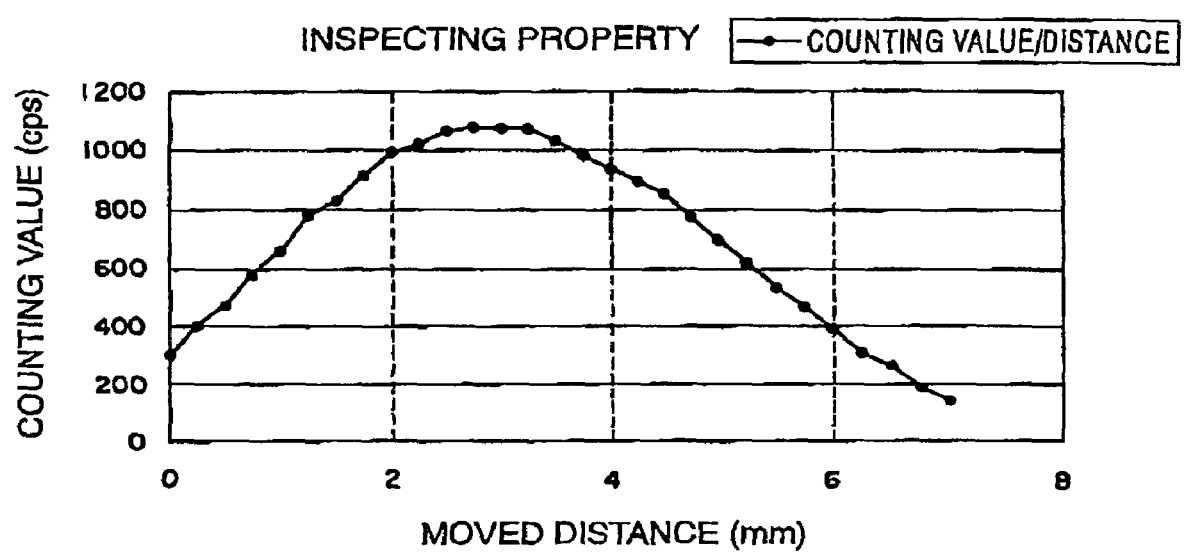
FIG. 8 is a graph showing the result of the detecting property obtained by the sensitivity test of the radiation detector shown in EXAMPLE 2.

The scintillator was placed on a plate to be in contact with the edge of the radiation source (85.8 Kbq/3 μl) and the plate was moved by every 0.25 mm along the axis of the scintillator. 1 point was measured for 10 seconds and the average measured counts per second was obtained. Only the result of the measurement performed on $^{89}$Sr is shown in FIG. 8.

3. Detection Scanning Test using Simulated Blood Vessel

Figure 9:
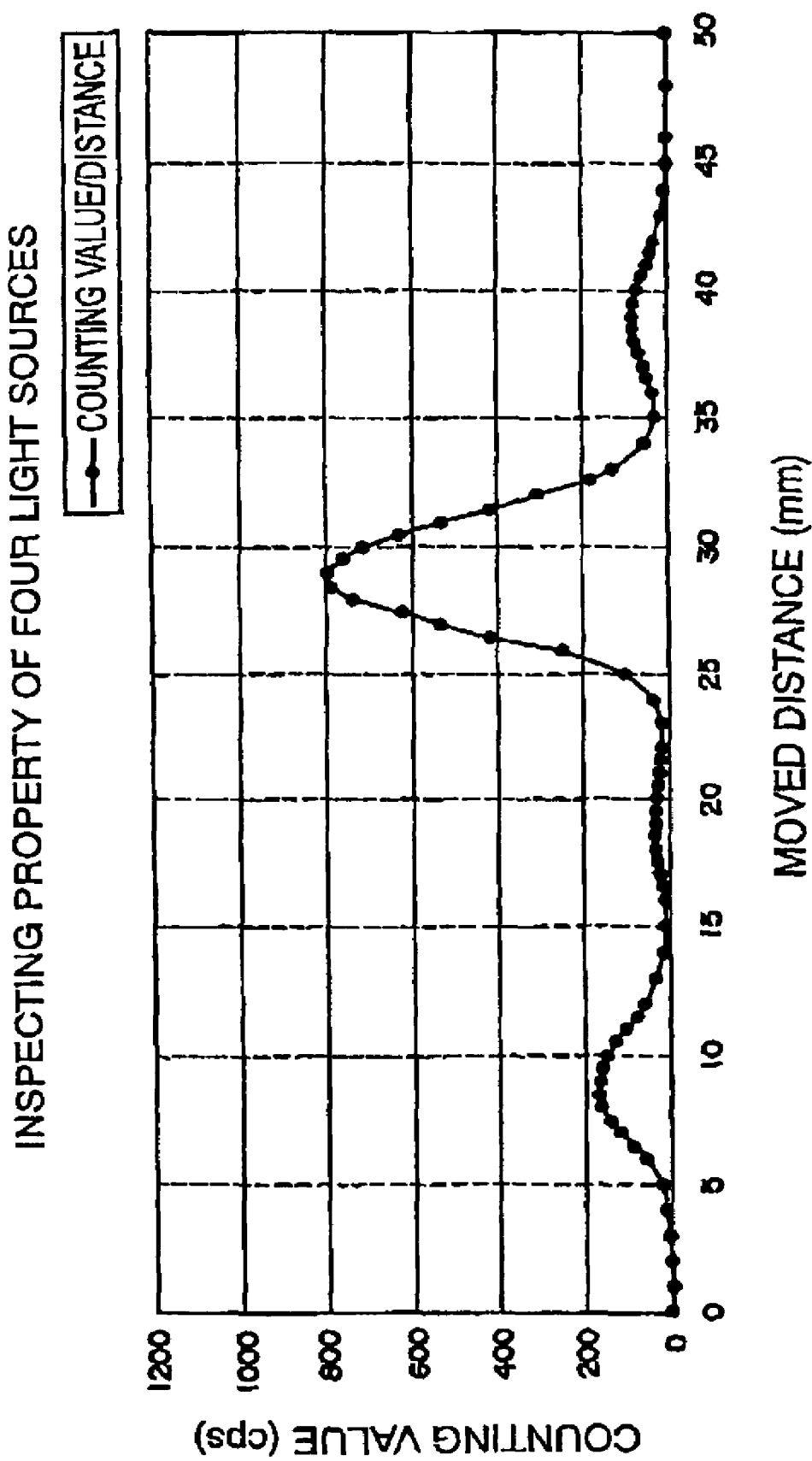
FIG. 9 is a graph showing the test result of the detection scanning obtained by the sensitivity test using simulated blood vessels.

A catheter (inner diameter of 1.57 mm, the thickness of 0.255 mm) was used as a simulated blood vessel and four plates with different dose of radiation were continuously placed on the external surface of the catheter. The radiation doses were set to be 16.9 KBq, 4.2 KBq, 84.5 KBq and 8.5 KBq and the volume was 3 μl for all. After inserting the scintillator inside the catheter, the detecting property was measured. In this case, 1 point was measured for 10 seconds and the average value per second was obtained. Only the result of the measurement performed on $^{89}$Sr is shown in FIG. 9.

4. Linearity of Radiation Dose and Counting Value

Figure 10:
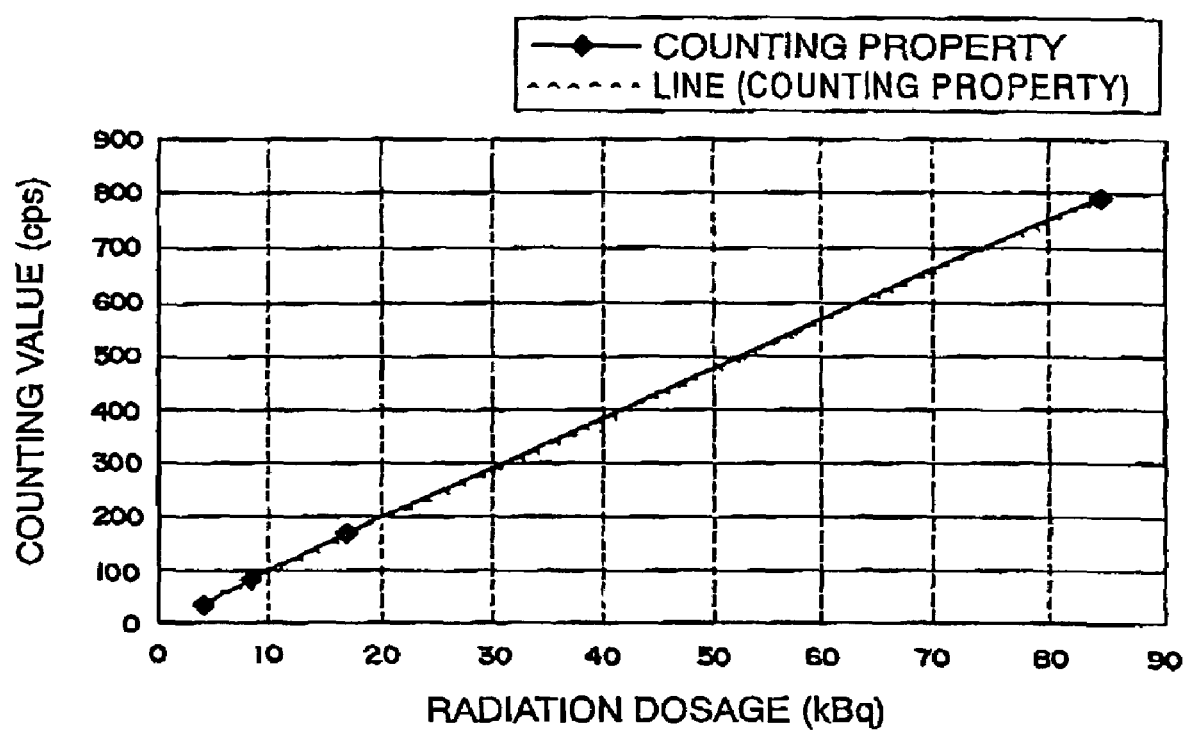
FIG. 10 is a graph showing the linearity of the counting values for the radiation source concentration gradient examined in the sensitivity test.

The linearity of the counting value against the concentration of $^{89}$Sr used on the above-described detection scanning test using the simulated blood vessel was examined. The results are shown in FIG. 10.

From the results of the above-described sensitivity tests, it has been clarified that the radiation detector of the present invention can make the background be the minimum and exhibits an excellent sensitivity for the gamma-ray and beta-ray. Especially, it exhibited an excellent sensitivity for beta-ray. Also, it has been concluded that it is possible to detect the radiation accumulation of gamma-ray since the comparison against the background was sufficiently large. The tests on the detecting property and the detection scanning using the simulated blood vessel were further performed on $^{89}$Sr. There were clear peaks for the radiation source positions in each test so that it has been verified that a small radiation accumulation such as the case of lesion inside the blood vessels can be detected. Also, there was almost linear relation between the radiation dose of the radiation source and the counting value so that the credibility of the measured value was verified.

INDUSTRIAL APPLICABILITY

As described, with the radiation detector of the present invention, it is possible to detect the radiation leakage from the tubules and radioactive substances accumulated in tissue inside a body by inserting a detection unit into the tubules or the blood vessels.

Specifically, the radiation detector of the present invention exhibits, for example, the following effects. Acute coronary syndromes (referred to as ACS in the followings) are especially serious diseases among heart diseases. Conventionally, it has been considered that ACS is caused by severe stenosis of coronary artery due to arteriosclerosis. However, recently, it has been clarified that ACS is caused without a significant stenosis. Lately, it is believed that ACS is caused by thrombus formation due to rapture of the plaque in the endothelium of the coronary artery and it is said to have a stronger relation with the properties of the plaque and the blood vessel endothelium covering the plaque than the degree of the stenosis of the coronary artery. Therefore, in order to predict possible ACS, it is most important to detect the plaque which is to be easily ruptured inside the coronary artery.

Recently, various detection devices have been tried to predict possible ACS. There is a report that the presence of the plaque can be recognized by tomogram of the coronary artery through the intravascular ultra sound. There is also a report that the presence of the plaque in the endothelium can be speculated by an eye observation of the inside the coronary artery through the intravascular endoscope. However, with these examinations, it is believed to be extremely difficult to predict the possible ACS. Both lack the information regarding the properties of the blood vessel endothelium and the plaque.

Originally, nuclear medicine method is an excellent method for recognizing the properties of the functions and tissue of the living body, since it is an examination in which the chemical substances reflecting the function and property are labeled by radiation and the accumulation and excretion are traced. However, as described, it has been impossible to detect a small lesion such as the one inside the coronary artery with the conventional nuclear medicine method.

On the contrary, with the radiation detector of the present invention, it is possible to detect the radiation accumulated in the plaque and thrombus by inserting the detection unit into the inside the coronary artery. Also, with the present invention, it is possible to identify the vulnerable plaque by administering a chemical substance for showing the properties of the blood vessel endothelium and the plaque as the radiopharmaceutical. It may be extremely a large contribution to medical technology when the possible ACS can be predicted by the present invention.

The invention claimed is:

1. A radiation detector for detecting a radioactive substance present in a tubule, or in the vicinity of said tubule comprising a detection unit having a bar-type scintillator which emits light by an incidence of radiation thereby transmitting the light from said scintillator through an optical fiber, wherein
said detection unit is formed in a size capable of being inserted into the tubule while a roughened surface is provided on the peripheral surface of said scintillator,
the diameter of said scintillator is set to be substantially 1.5 mm or less,
said optical fiber for transmitting the light from said scintillator is an optical fiber aggregation which is obtained by bundling up thin optical fibers to have substantially the same diameter as that of said scintillator,
said aggregation is divided into two optical fiber branches thereby dividing the light equally for transmitting to photomultipliers,
said photomultipliers receive said divided lights for converting and amplifying each of said light into electric signals, and
a counter circuit of a controller receives and counts said electric signals as pulse for obtaining coincidence.

2. A radiation detector for detecting a radioactive substance present in tissue in a body system, comprising a detection unit having a bar-type scintillator which emits light by an incidence of radiation thereby transmitting the light from the said scintillator through an optical fiber, wherein
said detection unit is formed in a size capable of being inserted into a blood vessel while a roughened surface is provided on the peripheral surface of said scintillator,
the diameter of said scintillator is set to be substantially 1.5 mm or less,
said optical fiber for transmitting the light from said scintillator is an optical fiber aggregation which is obtained by bundling up thin optical fibers to have substantially the same diameter as that of said scintillator,
said aggregation is divided into two optical fiber branches thereby dividing the light equally for transmitting to photomultipliers,
said photomultipliers receive said divided lights for converting and amplifying each of said light into electric signals, wherein
a counter circuit of a controller receives and counts said electric signals as pulse for obtaining coincidence.

3. The radiation detector according to claim 1 or claim 2, wherein a part of the top end face and the peripheral surface of said scintillator are covered by a radiopaque substance for determining the position of the scintillator using radiography.

4. The radiation detector according to claim 1 or claim 2, further comprising a rotary moving device for rotating and moving said detection unit back and forth in a tubule or inside a blood vessel.

* * * * *